United States Patent [19]  
Brisson et al.

[11] Patent Number: 4,693,247
[45] Date of Patent: Sep. 15, 1987

[54] TRIGGERING CIRCUIT

[75] Inventors: Alfred G. Brisson, Kildeer; Christopher Nowacki, Arlington Heights, both of Ill.

[73] Assignee: Trutek Research, Inc., Lake Zurich, Ill.

[21] Appl. No.: 912,959

[22] Filed: Sep. 29, 1986

[51] Int. Cl.[4] .............................................. A61B 17/00
[52] U.S. Cl. ..................................................... 128/328
[58] Field of Search ........................ 128/24 A, 328, 705, 128/670, 695, 700, 4.95

[56] References Cited

U.S. PATENT DOCUMENTS 4,595,019  6/1986  Shene et al. ......................... 128/328
4,620,545  11/1986  Shene et al. ....................... 128/24 A Primary Examiner—Henry J. Recla
Assistant Examiner—John P. Lacyk
Attorney, Agent, or Firm—Robert M. Wolters

[57] ABSTRACT

Apparatus is provided for the extracorporeal disintegration of kidney stones and the like. An ellipsoidal reflector has a spark gap positioned at one focus point of the ellipsoid, and the reflector is positioned so that the kidney stone being disintegrated is at the second focus point. The reflector is filled with water so that when a spark is generated through the spark gap, a shock wave is generated through which is focused through the water and through body tissues on the kidney stone. Both an electrocardiogram apparatus and an ultrasound pick-up apparatus are coupled to a spark triggering circuit controlling the pulse generator so that a spark or pulse can be generated only during ventricular contraction, thereby avoiding any possibility of inducing fibrillation of the heart.

5 Claims, 4 Drawing Figures

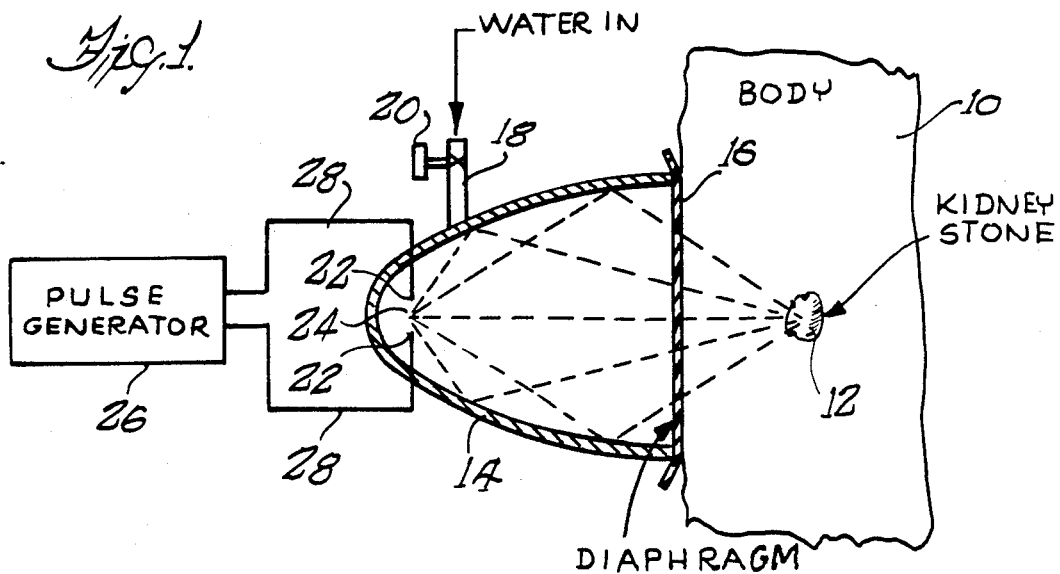
Fig. 1.
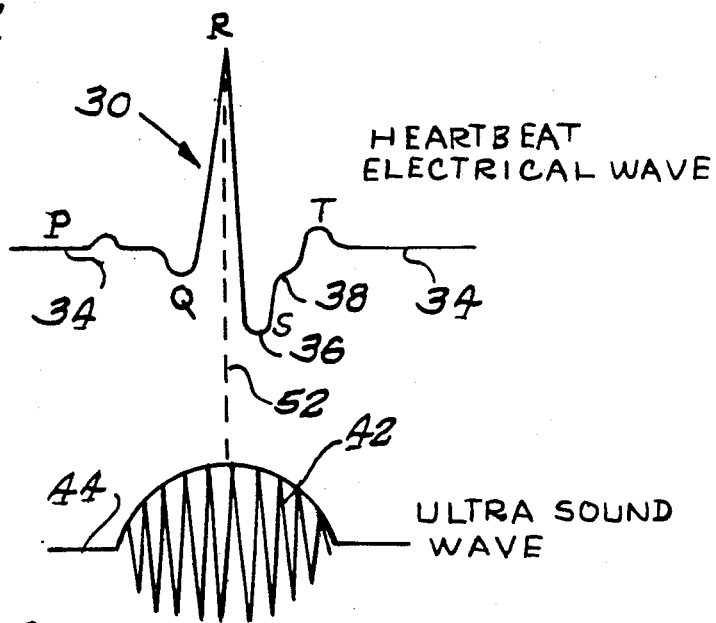
Fig. 2.
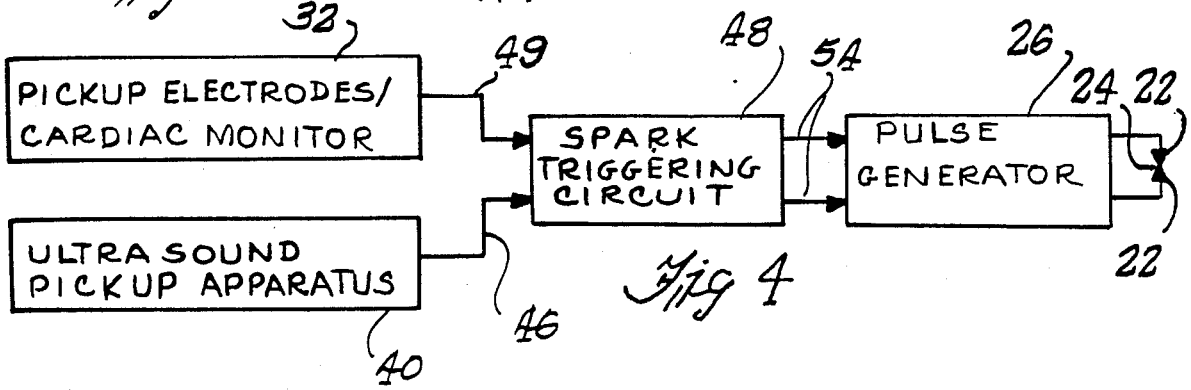
Fig. 3.
Fig. 4

TRIGGERING CIRCUIT

BACKGROUND OF THE INVENTION

The present invention relates to a triggering circuit for extracorporeal disintegration of kidney stones.

Kidney stones, and also naturally occuring stones in the bladder and the ureter can be exquisitely painful, and often require surgical relief. Excision or destruction of stones in the bladder and sometimes in the ureter can be relatively easily accomplished but removal of stones from the kidney is a major procedure.

Removal of stones from the kidney is a very serious and traumatic surgical procedure. A large incision is made in the body. The kidney is essentially removed from the body and cut open. The stone or stones are then removed, whereupon the kidney is sutured and returned to the body, with the body then being sutured.

Chemotherapy is available as a non-invasive therapy for uric acid stones. In this therapy the urine is alkalized. The existing stone thus is dissolved over a substantial period of time, and in most cases the patient can be cured before his condition becomes acute. However, the patient's condition is often already acute when the stone is discovered, and immediate surgery is imperative. Attempts at chemical dissolution of other types of stones have not been successful.

There are procedures for removing stones from the bladder which do not require cutting of the body. They are, however, invasive procedures in that the necessary devices are inserted through the urethra. In one of these procedures an electrohydraulic impulse is provided. A high energy capacitor is discharged by means of a coaxial electrode within the bladder, whereby a spark jumps between two poles of said electrode, establishing a hydrodynamic wave which destroys the concretion upon contact. The electrode thus must be in close proximity to the stone and a cystoscope having an optical telescope is utilized to visualize the spark generating electrodes.

As an alternative, ultrasonic waves on the order of 27 KHz. are used to disintegrate bladder stones. An optical device and an ultrasound converter are carried by a hollow steel probe which is inserted through the urethra. High frequency electrical energy is transformed into mechanical energy by an ultrasound converter and carried by the hollow steel probe which must be in contact with the bladder stone.

With both electrohydraulic impulses and ultrasonic disintegration of bladder stones it has been necessary for the energy source to be very close to or to effect physical contact with the stone. Such procedures are transuretheral and are routine for bladder stones. Ureteral stones and kidney stones recently have been fragmented by such techniques percutaneously. Such procedures are invasive, but do not involve major cutting of the body.

The percutaneous approach to ureteral and kidney stones has avoided the massive surgery outlined heretofore. A needle is inserted through the skin to the renal pelvis, the collecting area of the kidney. The needle is hollow and a guide wire is inserted through the needle into the kidney. The needle is then removed, and successively larger tubes are run in over the guide wire, leading up finally to a tube 8 mm in diameter. Viewing and stone cracking apparatus then are inserted through this tube to crack or disintegrate the stone. The approach is still invasive, and traumatic to the patient.

One approach has been made on an experimental basis of non-invasive breaking-up or disintegration of kidney stones in the body. Such non-invasive disintegration of kidney stones is disclosed in U.S. Pat. Nos. 3,942,531 to Hoff et al and 4,311,147 to Hausler. The first of these patents is exemplified in a machine commercially available in the Federal Republic of Germany from Dornier System GmbH. A few of the Dornier machines are now in the United States. Such machines are quite large since they require the patient to be immersed in a tub of water in a crouched, face-up position. Two dimensional X-ray procedures are utilized to determine the position of the stone by moving the patient. The machine includes an underwater spark gap shock wave generator which lies outside of the patient's body and at the first focal point of an ellipsoid. The patient is moved around in the water bath by servo mechanisms utilizing the two dimensional X-ray technique until the kidney stone is positioned at the second focal point of the ellipsoid. Since X-rays are used only radio opaque stones can be located. The shock wave is then generated, and passes through the water bath and through the patient's body to convey the energy to the kidney stone. The Dornier machine requires a 40 square meter room 3 meters in height. The machine base is six meters by one meter. The present cost of the machine, which may be expected to rise with inflation, is two million dollars, plus 10% of the price of the machine each year for a service contract. The service contract includes the cost of a technician who must be on hand at all times when the machine is in operation. It is contra-indicated if the ureter is blocked, since the material must pass out through the ureter. It is also unsuccessful with radio transparent or translucent stones, since they cannot be located by X-ray techniques. It must be emphasized that precise aiming of an external shock wave is necessary since energy focused into an air or gas pocket in the body can cause damage to interface tissue.

It has been found that if the shock wave is applied to the body other than during or immediately after ventricular contraction a few fibrillations of the heart have been produced. Such fibrillation obviously is to be avoided.

OBJECTS AND SUMMARY OF THE PRESENT INVENTION

It is an object of the present invention to provide extracorporeal disintegration of kidney stones by focused shock wave in which the shock wave is synchronized with beating of the heart to avoid fibrillation.

Particularly, it is an object of the present invention to utilize both an electrocardiograph and ultrasonic observation of heartbeat to prevent application of shock wave therapy for the destruction of kidney stones other than during ventricular contraction, and thereby to avoid fibrillation.

In achieving the foregoing and other objects of the present invention we use an ellipsoidal reflector filled with water and positioned against the patient's body. A spark gap device is provided at one focus of the reflector, and the reflector is positioned relative to the body so that the kidney stone or other calculus is positioned at the second focal point of the ellipsoidal reflector. A standard electrocardiogram is taken from the patient on a continuing basis. Furthermore, activity of the patient's heart is continually monitored by an ultrasound device.

The output of the ultrasound device and the output of the electrocardiogram apparatus are utilized together to ensure that a spark can be generated by the spark gap device only during the ventricular contraction of the heart, sometimes known as the QRS portion of the electrocardiogram. Interference with proper operation of the heart therefore is avoided, and fibrillation is positively precluded.

THE DRAWINGS

The present invention will be understood from the following description when taken in connection with the accompanying drawings wherein:

FIG. 1 is a fragmentary sectional view, partially schematic in nature, illustrating certain of the principles of the present invention;

FIG. 2 is the electrical wave produced by a heartbeat as seen in an electrocardiogram;

FIG. 3 is a representation of the audio frequency representation of the ultrasound wave of heart activity; and FIG. 4 is a block diagram illustrating the full principles of the present invention.

DETAILED DESCRIPTION OF THE ILLUSTRATED EMBODIMENT

Turning now to the drawings in greater particularity, and first to FIG. 1, there will be seen a portion of the human body 10 illustrated somewhat schematically. The body includes a kidney stone 12. It will be understood that the present invention could be utilized equally well to remove bladder stones and other concretions or calculi, but the removal of kidney stones and stones in the upper ureter is a more serious matter, and will be spoken of throughout.

An ellipsoidal reflector 14 is provided across its open end with a diaphragm 16 of elastomeric or plastic resin material, and is positioned against the body. The reflector is provided with water inlet 18 having a valve 20 through which the reflector is filled with water. A pair of electrodes 22 define a spark gap 24 at the first focal point of the ellipsoid. A pulse genertor 26 including a large capacitor and a voltage source is connected by means such as wires 28 to the electrodes 22.

Suitable aiming means is provided which may be a sonic aiming means or an X-ray aiming means, but the aiming means is not illustrated since it does not form a part of the present invention. In any event, the reflector is moved in accordance with the aiming means so that the kidney stone 12 lies at the second focus point of the ellipsoid of which the reflector 14 forms a part. It will be appreciated that the human body exhibits considerable resilience, whereby the reflector 14 can be advanced or retracted relative to the body to some degree. The reflector of course may be moved laterally of itself. For major positioning changes a bellowed mechanism or extensible diaphragm (not shown) or other extensible devices can be incorporated into the open end of the reflector.

The electrocardiogram of a normal heartbeat is shown at 30 in FIG. 2. The electrocardiogram mechanism or apparatus is quite conventional in nature and is applied to the patient in the usual fashion, and is shown only diagrammatically in FIG. 3 where the pick-up electrodes/cardiac monitor 32 are shown. The cardiac wave comprises a generally flat reference section 34 having pip P, and having a dip at Q. From the dip the electrocardiogram 30 rises rapidly to a peak at R, and drops off a negative pip 36 at S, rising with an inflection at 38 to a small positive pip at T, thereafter dropping to the reference line 34. The reference line 34 is shown as flat primarily for schematic purposes, and generally will have a slight waver to it. Atrial contraction takes place at P, and the QRS wave presents ventricular contraction. If the shock wave from the spark gap 24 is applied during the ventricular contraction, then it can have no effect on the heart, since the ventrical of the heart is already contracting. Thus, there is no danger of fibrillation at this time.

Similarly, a conventional ultrasound pick-up apparatus is shown diagramatically at 40 in FIG. 4. The ultrasound reading is continuous. The heart wall moves, and a Doppler Effect can be seen on reflection. A commercial ultrasound pick-up apparatus provides an audio wave representing the activity of the heart, and a pulse or burst of audio wave is provided at 42 during ventricular contraction, rising from a base line 44.

The ultrasound pick-up apparatus 40 is connected by means including a line 46 to a spark triggering circuit 48 and opens an electronic window during the time of the audio burst or pulse 42.

The pick-up electrodes/cardiac monitor 32 also are connected by means of a line 49 to the spark triggering circuit. As will be seen, the R peak of the heartbeat electrical wave appears substantially at the midpoint of the audio burst or pulse 42 as indicated by the vertical broken line 52. At the time the electrical wave reaches the R peak the window in the spark triggering circuit 50 is open, and therefore the electrical peak potential at R is passed through the spark generating circuit. The spark generating circuit is connected by means such as wires 54 to the pulse generator 26, and causes the pulse generator to generate a spark across the spark gap 24 only when the ventricular contraction is indicated by the window opened by the ultrasound wave, and by the transmission of the electrical wave peak at R.

Thus, in accordance with the present invention, double assurance is provided that the spark gap pulse wave will be generated only during ventricular contraction of the heart, whereby any possibility of fibrillation is positively avoided. The ultrasound wave provides a relatively wide window or timing space within which the pulse wave can be generated, but the pulse wave cannot be generated from that alone. It is necessary that the heartbeat electrical wave be disposed within the QRS portion of the heartbeat, and preferably at the R peak with the spark triggering circuit to effect pulse generation. As will be appreciated, a rather simple AND circuit is all that is necessary to insure this synchronization of the ultrasound and electrical waves. If for some reason the heartbeat electrical waves should produce a peak that might otherwise tend to produce a spark from the pulse generator, no spark can be produced if the ultrasound wave does not indicate ventricular contraction. There is thus double protection, through ultrasound and electrical waves to ensure that spark generation and the shock wave generated thereby can occur only during ventricular contraction of the heart of the patient.

The specific example of the invention as herein shown and described is for illustrative purposes only. Various changes in structure will no doubt occur to those skilled in the art, and will be understood as forming a part of the present invention insofar as they fall within the spirit and scope of the appended claims.

The invention is claimed as follows:

1. The combination for the extracorporeal disintegration of calculi such as kidney stones comprising a reflector having a fluid therein adapted to be coupled to a body having a heart and a calculus such as a kidney stone, means in said reflector for generating a wave in said fluid, said reflector being positioned to focus said wave on said calculus in said body, ultrasound means for detecting when said heart is undergoing a ventricular contraction, electrocardiogram means for detecting when said heart is undergoing a ventricular contraction, a triggering circuit for operating said wave generating means to generate a calculus disintegrating wave, and means connecting said ultrasound means and said electrocardiogram means to said triggering means to operate said wave generating means only when ventriculating contraction is detected by both of said ultrasound means and said electrocardiogram means.

2. The combination as set forth in claim 1 wherein the wave generating means comprises means for generating a shock wave.

3. The combination as set forth in claim 2 wherein the shock wave generating means comprises means providing a spark gap, and means for discharging a spark across said gap.

4. The combination as set forth in claim 1 wherein said electrocardiogram indicates a PQRST wave, and wherein said ultrasound means is effective substantially throughout said PQRST wave, and wherein said electrocardiogram means is effective only in the QRS portion of the wave to cause said triggering means to operate said wave generating means.

5. The combination as set forth in claim 4 wherein said electrocardiogram means is operated substantially at the R portion of the wave to cause said triggering means to operate said wave generating means.

* * * * *